United States Patent [19]

Michel et al.

[11] 4,177,265

[45] Dec. 4, 1979

[54] PROCESS FOR THE PURIFICATION OF AMPHOTERICIN B AND A SOLUBILIZING MEDIA USEFUL IN THAT PROCESS

[75] Inventors: Gerd W. Michel, Princeton; Elizabeth A. Fralick, North Brunswick, both of N.J.

[73] Assignee: E. R. Squibb & Sons, Inc., Princeton, N.J.

[21] Appl. No.: 773,584

[22] Filed: Mar. 2, 1977

[51] Int. Cl.² .................. A61K 31/71; A61K 35/00
[52] U.S. Cl. .................. 424/181; 536/17 R; 424/119; 424/123
[58] Field of Search .................. 424/123, 119, 181; 536/17

[56] References Cited

U.S. PATENT DOCUMENTS 2,908,611  10/1959  Dutcher et al. .................. 424/119

FOREIGN PATENT DOCUMENTS 1298172  5/1971  United Kingdom .................. 424/123

*Primary Examiner*—Jerome D. Goldberg
*Attorney, Agent, or Firm*—Lawrence S. Levinson; Donald J. Barrack

[57] ABSTRACT

Acetone or methanol saturated with sodium iodide or sodium thiocyanate are useful solubilizing media for amphotericin B.

13 Claims, No Drawings

PROCESS FOR THE PURIFICATION OF AMPHOTERICIN B AND A SOLUBILIZING MEDIA USEFUL IN THAT PROCESS

BACKGROUND OF THE INVENTION

Amphotericin B, a potent antifungal agent, is a member of a class of compounds known as polyene macrolide antibiotics. These compounds are characterized by a large lactone ring which includes a chain of conjugated double bonds.

Amphotericin B, and its method of preparation from *Streptomyces nodosus*, is disclosed by Dutcher et al. in U.S. Pat. No. 2,908,611, issued Oct. 13, 1959. The structure of amphotericin B is now known to be

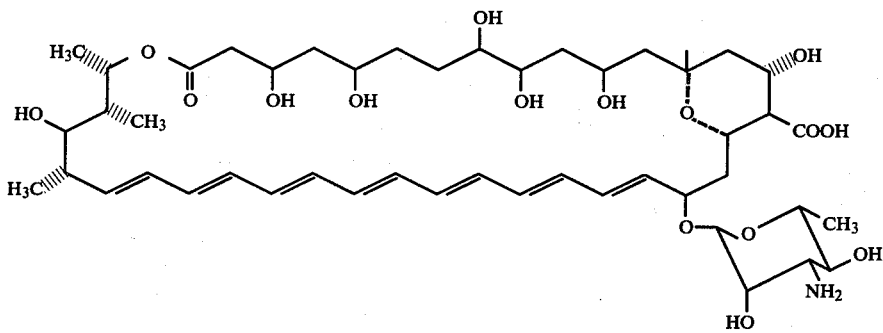

Nystatin is another member of the group of antibiotics known as polyene macrolides. Mendelsohn, in U.S. Pat. No. 3,509,255, issued Apr. 28, 1970, discloses a process for the purification of nystatin which comprises extracting crude nystatin with acetone which is saturated with sodium iodide, sodium thiocyanate, potassium thiocyanate, ammonium thiocyanate, or mixtures thereof, and precipitating purified crystalline nystatin from the extract by the displacement of acetone with water.

The solubility characteristics of nystatin and amptericin B differ markedly. While it is known that polyene macrolides have a very limited solubility in common organic solvents, nystatin is, in general, substantially more soluble than amphotericin B, specifically in such commercially attractive solvents as acetone and methanol. The solubility of amphotericin B in acetone is about 95 γ/ml and in methanol about 940 γ/ml. The problems caused by this lack of solubility are well known to those who work with processes for the isolation and extraction of amphotericin B.

As recognized by Dutcher et al. in U.S. Pat. No. 2,908,611 amphotericin B does have good solubility in dimethylformamide and glacial acetic acid. Furthermore, the solubility of amphotericin B in the lower alkanols can be increased by the addition of acid or strong base. In view of the above, it is not surprising that the prior art has relied heavily on the use of dimethylformamide in processes for the purification of amphotericin B.

SUMMARY OF THE INVENTION

It is an object of this invention to provide a useful solubilizing medium for amphotericin B.

It is an object of this invention to provide a solubilizing medium which can be used in a process for the purification of amphotericin B which yields a crystalline product.

It is an object of this invention to provide a solubilizing medium which can be used in a process for the purification of amphotericin B which yields a product of high purity and high potency.

It is an object of this invention to provide a solubilizing medium which can be used in a process for the purification of amphotericin B that does not necessitate the making of pH adjustments.

It is an object of this invention to provide a solubilizing medium which can be used in a process for the purification of amphotericin B that can be carried out mostly at room temperature.

It has now been found that acetone or methanol saturated with sodium iodide or sodium thiocyanate are useful solubilizing media for amphotericin B.

DETAILED DESCRIPTION OF THE INVENTION

The solubility of amphotericin B in either acetone or methanol is markedly increased by saturating the solvent with sodium iodide or sodium thiocyanate. The following table presents the solubility of amphotericin B in acetone and in methanol, with and without each of the sodium iodide and sodium thiocyanate additives. When the additive is present, it is present in such an amount as to yield a saturated solution of the solvent.

| Solubility of Amphotericin B | (γ/ml) | |
|---|---|---|
| | Acetone | Methanol |
| No additive | 95 | 940 |
| Sodium iodide | 61,522 | 52,368 |
| Sodium thiocyanate | 22,115 | 52,282 |

The above described solubilizing media for amphotericin B make possible the use of a relatively simple process for the purification of amphotericin B. The process comprises the following steps:

(i) Dissolve crude, partially purified or contaminated amphotericin B in acetone or methanol saturated with sodium iodide or sodium thiocyanate;
(ii) Separate the resultant extract mixture from insoluble constituents;
(iii) Combine the amphotericin B with a solvent mixture comprising N,N-dimethylformamide, methanol, and water;
(iv) Crystallize the amphotericin B; and
(v) Recover the crystalline product.

The amphotericin B employed as the starting material in the purification process may include crude, partially purified or contaminated amphotericin B. The expression "contaminated amphotericin B" is meant to include not only amphotericin B that contains chemical contaminants but is also meant to include physical contaminants such as dirt particles, fibrous material and other particulate elements that might cause amphotericin B to be unacceptable for pharmaceutical utility.

The first step of the purification process is the extraction of the amphotericin B starting material by suspending it in acetone or methanol saturated with sodium iodide or sodium thiocyanate. The extraction step can be carried out by adding together the materials in any order. Temperature is not critical and the extraction will preferably be carried out at room temperature. The amount of salt saturated acetone or methanol solution is not critical, but should be sufficient to dissolve the amphotericin B.

Separation of the extract mixture is carried out using procedures well known in the art. Preferably, filtration will be used to separate out the amphotericin B extract from insoluble materials.

Combining the purified amphotericin B extract with a solvent mixture of N,N-dimethylformamide, methanol and water results in the precipitation of amorphous material. The resulting slurry provides a suitable environment for promoting the transformation of amphotericin B to a crystalline material.

The slurry of amorphous amphotericin B is converted to crystalline material by heating at a temperature of about 40° C. to about 60° C., preferably about 45° C. to about 55° C. Optionally, small amounts of seed crystals may be added to the slurry to accelerate crystallization.

Recovery of crystalline amphotericin B can be accomplished using conventional procedures; e.g., centrifugation or filtration. The isolated material can be washed with a suitable solvent, if desired, prior to drying. Exemplary solvents for the washing step are acetone; mixtures of acetone and water; methanol; mixtures of methanol and water; water; or combinations thereof.

The following examples are illustrative of the process of this invention.

EXAMPLE 1

To a 150 ml beaker are added 4.24 g of amphotericin B (800 $\gamma$/mg-microbiological assay) and 55 ml of acetone. A total of 22.41 g of sodium iodide is added with stirring over a 60-minute period; the extraction mixture is filtered, and the filter cake is washed with 25 ml of acetone. The filtrate and wash are added to a 50°-52° C. solvent mixture comprised of 98 ml of N,N-dimethylformamide, 44.6 ml of water, 49.4 ml of methanol, and 20 mg of amphotericin B seed crystals; the slurry is maintained at 50°-52° C. for 10 minutes after the completion of addition to ensure total conversion to a crystalline product. After cooling the slurry to 5° C. and storing for about 16 hours, the purified product is collected by filtration, washed with 50 ml of 75% aqueous methanol, and dried under vacuum at 40°-45° C. for 6 hours. The yield is 3.35 g of crystalline amphotericin B assaying 962 $\gamma$/mg (microbiological assay).

EXAMPLE 2

To a 150 ml beaker are added 4.24 g of amphotericin B (800 $\gamma$/mg-microbiological assay) and 55 ml of methanol. A total of 71.88 g of sodium thiocyanate is added with stirring over a 60-minute period; the extraction mixture is filtered, and the filter cake is washed with 25 ml of methanol. The rich filtrate and wash are added to a 50°-52° C. solvent mixture comprised of 98 ml of N,N-dimethylformamide, 44.6 ml of water, 49.4 ml of methanol, and 20 mg of amphotericin B seed crystals; the slurry is maintained at 50°-52° C. for 10 minutes after the completion of addition to ensure total conversion to a crystalline product. After cooling the slurry to 5° C. and storing for about 16 hours, the purified product is collected by filtration, washed with 50 ml of 75% aqueous methanol, and dried under vacuum at 40°-45° C. for 6 hours. The yield is 1.92 g of crystalline amphotericin B assaying 903 $\gamma$/mg (microbiological assay).

What is claimed is:

1. An amphotericin B composition comprising a solution of amphotericin B in a salt saturated solution of acetone or methanol, wherein the salt is sodium iodide or sodium thiocyanate.

2. An amphotericin B composition in accordance with claim 1 wherein the salt saturated solution is a saturated solution of sodium iodide in acetone.

3. An amphotericin B composition in accordance with claim 1 wherein the salt saturated solution is a saturated solution of sodium thiocyanate in acetone.

4. An amphotericin B composition in accordance with claim 1 wherein the salt saturated solution is a saturated solution of sodium iodide in methanol.

5. An amphotericin B composition in accordance with claim 1 wherein the salt saturated solution is a saturated solution of sodium thiocyanate in methanol.

6. A process for the purification of amphotericin B which comprises:
   (i) forming a solution of amphotericin B in a salt saturated solution wherein the salt is sodium iodide or sodium thiocyanate and the solvent is acetone or methanol;
   (ii) separating out amphotericin B extract from insolubles;
   (iii) combining the amphotericin B extract with a solvent mixture comprising N,N-dimethylformamide, methanol, and water;
   (iv) heating the slurry of amorphous material to form crystalline amphotericin B; and
   (v) recovering the crystalline amphotericin B.

7. A process in accordance with claim 6 wherein the salt saturated solution is a saturated solution of sodium iodide in acetone.

8. A process in accordance with claim 6 wherein the salt saturated solution is a saturated solution of sodium thiocyanate in acetone.

9. A process in accordance with claim 6 wherein the salt saturated solution is a saturated solution of sodium iodide in methanol.

10. A process in accordance with claim 6 wherein the salt saturated solution is a saturated solution of sodium thiocyanate in methanol.

11. A process in accordance with claim 6 wherein filtration is used to separate amphotericin B from the extract mixture.

12. A process in accordance with claim 6 wherein the amorphous amphotericin B is heated at a temperature of about 40° to about 60° to convert it to crystalline amphotericin B.

13. A process in accordance with claim 6 wherein seed crystals are used to accelerate crystallization.

* * * * *